US012139452B2

(12) United States Patent
Bonrath et al.

(10) Patent No.: US 12,139,452 B2
(45) Date of Patent: Nov. 12, 2024

(54) PROCESS FOR THE PRODUCTION OF RETINAL

(71) Applicant: DSM IP ASSETS B.V., Heerlen (NL)

(72) Inventors: Werner Bonrath, Kaiseraugst (CH); Marc-André Mueller, Kaiseraugst (CH); Bettina Wuestenberg, Kaiseraugst (CH); Viktor Zimmermann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 501 days.

(21) Appl. No.: 17/603,184

(22) PCT Filed: Apr. 3, 2020

(86) PCT No.: PCT/EP2020/059479
§ 371 (c)(1),
(2) Date: Oct. 12, 2021

(87) PCT Pub. No.: WO2020/212164
PCT Pub. Date: Oct. 22, 2020

(65) Prior Publication Data
US 2022/0204445 A1 Jun. 30, 2022

(30) Foreign Application Priority Data
Apr. 15, 2019 (EP) ..................... 19169201

(51) Int. Cl.
C07C 403/08 (2006.01)
C07C 403/14 (2006.01)
(52) U.S. Cl.
CPC .......... *C07C 403/14* (2013.01); *C07C 403/08* (2013.01)

(58) Field of Classification Search
None
See application file for complete search history.

(56) References Cited

U.S. PATENT DOCUMENTS

| 4,209,644 | A | 6/1980 | Ichikawa et al. |
| 5,243,094 | A | 9/1993 | Borg |
| 5,447,959 | A | 9/1995 | Borg |
| 2021/0309596 | A1* | 10/2021 | Rey ........................ C07C 29/14 |

FOREIGN PATENT DOCUMENTS

| GB | 1 482 614 | 8/1977 |
| JP | S51052102 A | 10/1974 |
| JP | S58038228 A | 3/1983 |
| JP | H04502167 A | 4/1992 |
| WO | 02/092560 | 11/2002 |
| WO | 03/037856 | 5/2003 |

OTHER PUBLICATIONS

Duhamel, L. et al. "The OSM (oxidation state modification) concept: Application to a new and rapid synthesis of retinoids" Tetrahedron Letters, vol. 35, No. 8, pp. 1209-1210, 1994 (Year: 1994).*
Julián Bergueiro, et al., "Synthesis of 11-cis-Retinoids by Hydrosilylation-Protodesilylation of an 11,12-Didehydro Precursor: Easy Access to 11- and 12-Mono- and 11,12-Dideuteroretinoids", Chemistry—A European Journal, vol. 18, No. 44, Sep. 20, 2012, pp. 14100-14107 (8 pages).
International Search Report and Written Opinion of the ISA for PCT/EP2020/059479 dated Jun. 22, 2020, 14 pages.
First Office Action, CN Application No. 202080028176.1, Sep. 20, 2023.

* cited by examiner

*Primary Examiner* — Medhanit W Bahta
(74) *Attorney, Agent, or Firm* — NIXON & VANDERHYE P.C.

(57) ABSTRACT

The present invention relates to a new process for the production of retinal or hydrogenated form of retinal.

14 Claims, No Drawings

PROCESS FOR THE PRODUCTION OF RETINAL

This application is the U.S. national phase of International Application No. PCT/EP2020/059479 filed Apr. 3, 2020 which designated the U.S. and claims priority to EP patent application Ser. No. 19/169,201.1 filed Apr. 15, 2019, the entire contents of each of which are hereby incorporated by reference.

The present invention relates to a new process to produce retinal and a hydrogenated form of retinal.

Retinal, which is also known as i.e. retinene, retinaldehyde and vitamin A aldehyde, is the compound of the following formula (Ia)

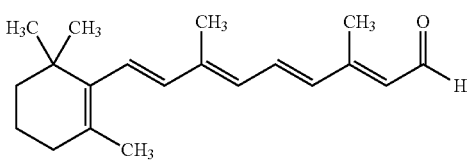

The specific hydrogenated form of retinal, which can also be produced according to the process of the present invention, is the compound of the following formula (b)

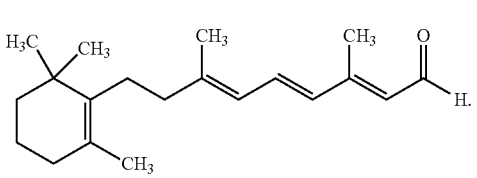

The compounds, which are produced by the process of the present invention can be summarized by the following formula (I)

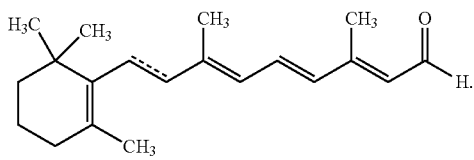

Due to the C—C double bonds, the compounds of formula (I) as well as the compounds of formula (II) can have several stereochemical isomers, which are not all implicitly drawn in this application, but which are also covered by the process according to the present invention. The effect of the stereochemistry is not essential for the process according to the invention.

Retinal and the hydrogenated form (compound of formula (Ib)) can be used as such or it is used as an intermediate in organic syntheses (i.e for the production of retinol or retinoic acid).

From Y. Shvo, et al (J. Org. Chem. 1998, 63, 5640) similar dehydrogenations are known, but the yield obtained therein are low and the applied oxidant is not industrially feasible and generates stochiometric amounts of waste.

Due to the importance of retinal and the hydrogenated form (especially in the Vitamin A synthesis), there is always a need to provide new processes for the production of the compounds of formula (I).

Surprisingly, it was found that the retinal can be produced by the dehydrogenation of the compound of formula (II))

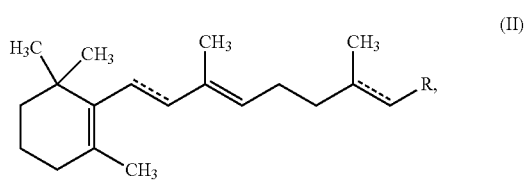

wherein R is —CHO or —CH$_2$OH.

This process is easy to handle, and it allows to provide a possibility to shorten the synthesis of vitamin A (and its derivatives).

Below are the routes to obtain Vitamin A (acetate) from the compounds of formula (IIa) and (IIb):

Route to obtain Vitamin A acetate from compounds (IIa)

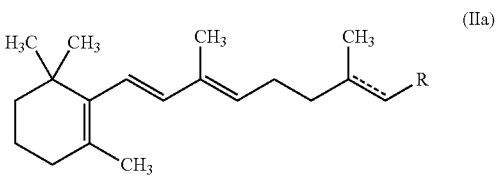

↓

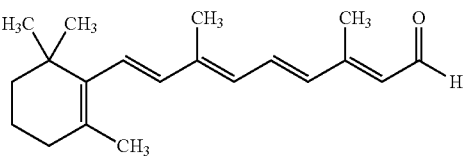

↓

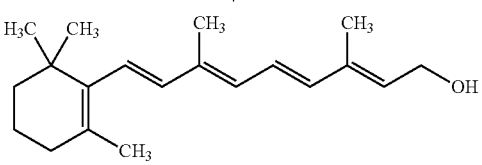

↓

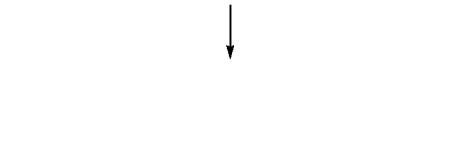

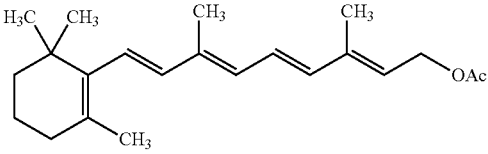

Vitamin A acetate

Route to obtain Vitamin A acetate from compounds (IIb)

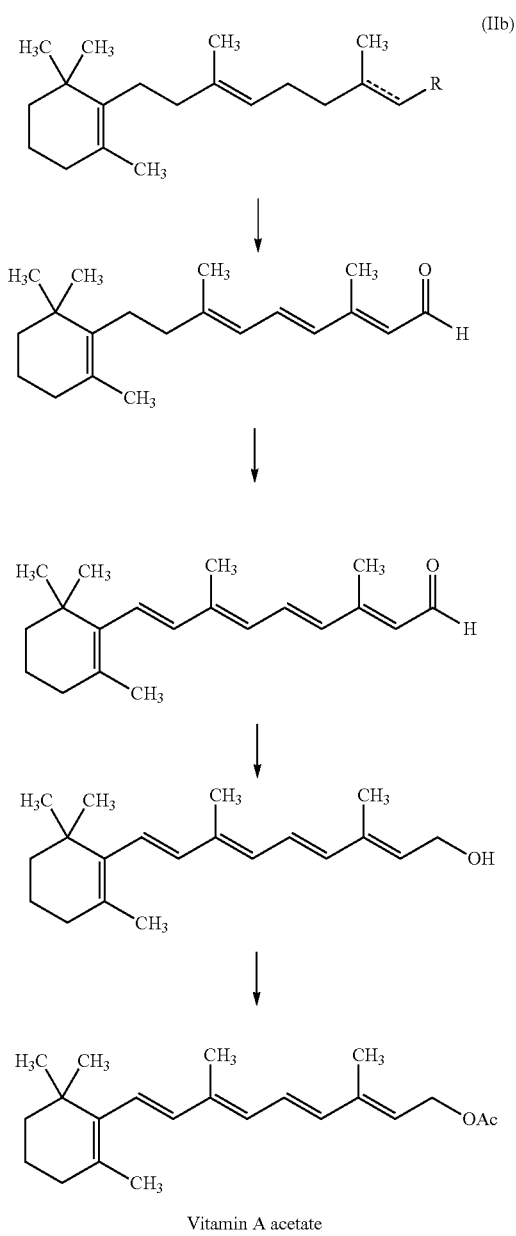

Vitamin A acetate

The routes to obtain vitamin A acetate starting from the hydrogenated forms (II'), (II''), (II'''), and (II'''') are similar to the one with compound (IIa) and of formula (IIb).

The process of the present invention is carried out in the presence of a transition metal catalyst. Especially in the presence of a Pd catalyst. Especially a Pd(II) catalyst. Very suitable is Pd(OAc)$_2$ as a catalyst.

The ligand of the transition metal catalyst can be changed (replacing OAc). But the ligand does not play a dominant role in the process.

Furthermore, the reaction can be carried out in the presence of air and/or O$_2$ as an oxidant.

The air and/or O$_2$ can be added constantly during to the process or at any suitable point in time of the reaction.

Therefore, the present invention relates to a process (P) for the production of the compound of formula (I)

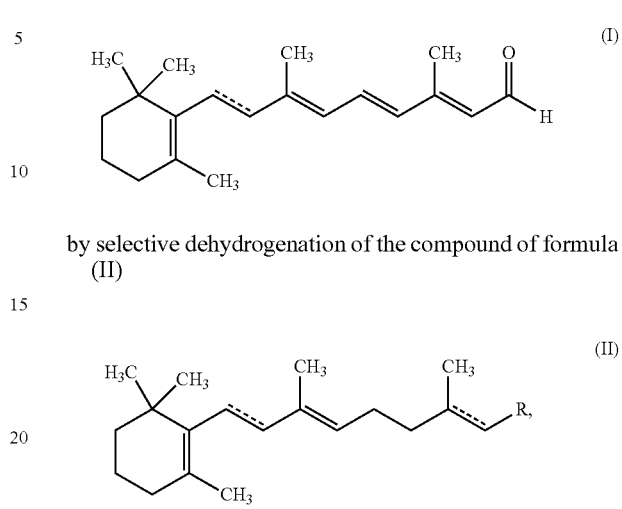

by selective dehydrogenation of the compound of formula (II)

wherein R is —CHO or —CH$_2$OH, and
wherein the dehydrogenation is carried out in the presence of at least one transition metal catalyst.

Furthermore, the present invention relates to process (P'), which is process (P), wherein the transition metal catalyst is a Pd catalyst.

Furthermore, the present invention relates to process (P''), which is process (P), wherein the transition metal catalyst is a Pd(II) catalyst; most preferably in the presence of Pd(OAc)$_2$.

Furthermore, the present invention relates to process (P'''), which is process (P), wherein the transition metal catalyst is Pd(OAc)$_2$.

The amount of the catalyst used in the process according to the present invention can vary. The amount of the catalyst usually goes from 0.01 mol-equivalent up to 0.5 mol-equivalent (in relation to compound of formula (II)).

Therefore, the present invention relates to process (P1), which is process (P), (P'), (P'') or (P'''), wherein the amount of the catalyst goes from 0.01 mol-equivalent up to 0.5 mol-equivalent (in relation to compound of formula (II)).

Furthermore, the process of the present invention can be carried out in the presence of air and/or O$_2$.

Therefore, the present invention relates to process (P2), which is process (P), (P'), (P''), (P''') or (P1), wherein the process is carried out in the presence of air and/or O$_2$.

The process according to the present invention is usually carried out in the presence of at least one base. Such as for example K$_2$CO$_3$, pyridine etc. The amount of the base can vary. It goes usually from 0.01 mol-equivalent up to 0.5 mol-equivalent (in relation to compound of formula (II)).

Therefore, the present invention relates to process (P3), which is process (P), (P'), (P''), (P'''), (P1) or (P2), wherein the process is carried out in the presence of at least one base.

Therefore, the present invention relates to process (P3'), which is process (P3), wherein the base is K$_2$CO$_3$ or pyridine.

Therefore, the present invention relates to process (P3''), which is process (P3) or (P3'), wherein the base is present in an amount of 0.01 mol-equivalent up to 0.5 mol-equivalent (in relation to compound of formula (II)).

The reaction is usually carried out in an inert solvent. The solvent is usually polar aprotic such as dimethylformamide (DMF).

Therefore, the present invention relates to process (P4), which is process (P), (P'), (P''), (P'''), (P1), (P2), (P3), (P3') or (P3''), wherein the process is carried out in an inert solvent.

Therefore, the present invention relates to process (P4'), which is process (P4), wherein the inert solvent is DMF.

The process according to the present is usually carried out at elevated temperatures. Usually the process according to the present invention is carried out at a temperature of from 0° C.-100° C., preferably from 5° C.-90° C.

Therefore, the present invention relates to process (P5), which is process (P), (P'), (P''), (P'''), (P1), (P2), (P3), (P3'), (P3''), (P4) or (P4'), wherein the process is carried out at a temperature of from 0° C.-100° C.

Therefore, the present invention relates to process (P5'), which is process (P5), wherein the process is carried out at a temperature of from 5° C.-90° C.

Furthermore, the present invention relates to the following new compound:

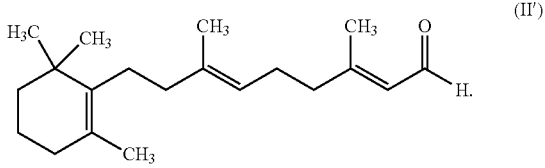

(II')

This new compound (7,8,11,12-tetrahydroretinal) can be obtained via oxidation of the corresponding allylic alcohol obtained via A. Proszenyák et al. Arch. Pharm. 2007, 340, 625-634.

Furthermore, the present invention relates to the following new compounds the of formulae

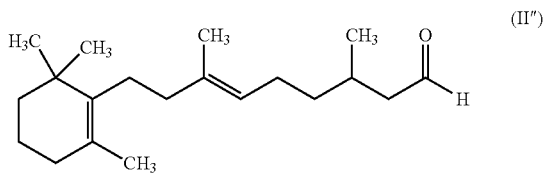 [SMILES: CC1=C(CC/C(C)=C/CCC(C)CC=O)C(C)(C)CCC1]

(II'')

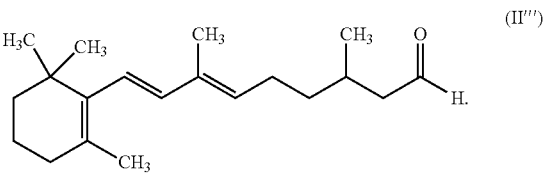

(II''')

These new compounds are produced via isomerization following a procedure of e.g. Mazet et al (Acc. Chem. Re. 2016, 49, 1232-1241) starting from 11,12-dihydro-retinal obtained via e.g. S. Saito, H. Yamamoto, J. Org. Chem. 1996, 61, 2928-2929) or 7,8,11,12-tetrahydroretinal.

As stated above the process according to the present invention is one important step in the synthesis of vitamin A (and/or its derivatives).

The following examples serve to illustrate the invention. The temperature is given in ° C. and all percentages are related to the weight.

EXAMPLES

Example 1

A 2-necked flask equipped with a stirring bar, thermometer and a dimroth condenser was charged with $K_2CO_3$ (16 mg, 0.15 eq), Pd(OAc)$_2$ (16 mg), 11,12-dihydroretinal (190 mg, 1.0 eq), DMF (3.0 mL) and pyridine (5 µL, 0.1 eq). The yellow suspension was stirred at 60° C. for 6 h, applying a constant air stream. The reaction mixture was cooled to room temperature and diluted with Et$_2$O (10 mL) and washed with H$_2$O (10 mL×3). The organic phase was concentrated under reduced pressure (40° C./30 mbar). Purification by column chromatography afforded the product as orange solid (85 mg, yield 46%).

Example 2

A 4-necked flask equipped with a stirring bar, thermometer and a dimroth condenser was charged with $K_2CO_3$ (150 mg, 0.17 eq), Pd(OAc)$_2$ (150 mg), 7,8,11,12-tetrahydroretinal (1.8 g, 1.0 eq). DMF (30.0 mL) and pyridine (50 µL, 0.1 eq). The yellow suspension was stirred at 60° C. for 6.5 h, applying a constant air stream. The reaction mixture was cooled to room temperature and diluted with Et$_2$O (100 mL) and washed with H$_2$O (100 mL×3). The organic phase was concentrated under reduced pressure (40° C./30 mbar). Purification by column chromatography afforded the product (11,12-dihydroretinal) as orange oil (0.66 g, yield 40%).

Example 3

A 3-necked flask equipped with a stirring bar, thermometer and a dimroth condenser was charged with $K_2CO_3$ (166 mg, 0.17 eq), Pd(OAc)$_2$ (189 mg), 11,12-dihydroretinol (2.1 g, 1.0 eq), DMF (30.0 mL) and 1,2-bis(diphenylphosphino)-ethane (416 mg, 0.14 eq). The yellow suspension was stirred at 60° C. for 6 h, applying a constant air stream. The reaction mixture was cooled to room temperature and diluted with Et$_2$O (100 mL) and washed with H$_2$O (100 mL×3). The organic phase was concentrated under reduced pressure (40° C./30 mbar). Purification by column chromatography afforded the product as orange solid (0.39 g, yield 18%).

Example 4

A 3-necked flask equipped with a stirring bar thermometer and a dimroth condenser was charged with $K_2CO_3$ (168 mg, 0.16 eq), Pd(OAc)$_2$ (190 mg), 7,8,11,12-tetrahydroretinol (2.2 g, 1.0 eq), DMF (30.0 mL) and 1,2-bis(diphenylphosphino)ethane (418 mg, 0.14 eq). The yellow suspension was stirred at 60° C. for 24 h, applying a constant air stream. The reaction mixture was cooled to room temperature and diluted with Et$_2$O (100 mL) and washed with H$_2$O (100 mL×3). The organic phase was concentrated under reduced pressure (40° C./30 mbar). Purification by column chromatography afforded the product (7,8-dihydroretinal) as orange oil (0.45 g, yield 21%).

Example 5

A 2-necked flask equipped with a stirring bar (1.5 cm) and a dimroth condenser was charged with $K_2CO_3$ (16 mg, 0.18 eq), Pd(OAc)$_2$ (23 mg), 7,8,11,12,13,14-hexahydroretinal (250 mg, 1.0 eq), DMF (3.0 mL) and pyridine (7 µL, 0.1 eq). The yellow suspension was stirred at 60° C. for 31 h, applying a constant air stream. The reaction mixture was cooled to room temperature and diluted with Et₂O (10 mL) and washed with H₂O (10 mL×3). The organic phase was concentrated under reduced pressure (40° C./30 mbar). Purification by column chromatography afforded the product as orange oil (48 mg, yield 19%).

Example 6

A 2-necked flask equipped with a stirring bar (1.5 cm) and a dimroth condenser was charged with K₂CO₃ (18 mg, 0.18 eq), Pd(OAc)₂ (18 mg), 11,12,13,14-tetrahydroretinal (200 mg, 1.0 eq), DMF (3.0 mL) and pyridine (6 μL, 0.1 eq). The yellow suspension was stirred at 60° C. for 48 h, applying a constant air stream. The reaction mixture was cooled to room temperature and diluted with Et₂O (10 mL) and washed with H₂O (10 mL×3). The organic phase was concentrated under reduced pressure (40° C./30 mbar). Purification by column chromatography afforded the product as orange solid (29 mg, yield 15%).

The invention claimed is:

1. A process for the production of a compound of formula (I):

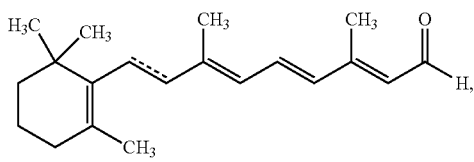

(I)

wherein the process comprises conducting selective dehydrogenation of a compound of formula (II):

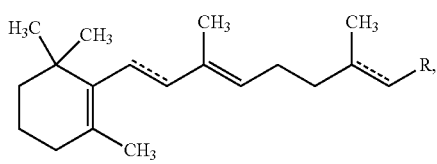

(II)

wherein R is —CHO or —CH₂OH,
wherein the selective dehydrogenation is carried out in the presence of at least one transition metal catalyst.

2. The process according to claim 1, wherein the transition metal catalyst is a Pd catalyst.

3. The process according to claim 1, wherein the transition metal catalyst is Pd(OAc)₂.

4. The process according to claim 1, wherein the catalyst is present in an amount from 0.01 mol-equivalent to 0.5 mol-equivalent in relation to the compound of formula (II).

5. The process according to claim 1, wherein the process is carried out in the presence of air and/or O₂.

6. The process according to claim 1, wherein the process is carried out in the presence of at least one base.

7. The process according to claim 6, wherein the at least one base comprises K₂CO₃ or pyridine.

8. The process according to claim 6, wherein the at least one base is present in an amount of 0.01 mol-equivalent to 0.5 mol-equivalent in relation to the compound of formula (II).

9. The process according to claim 1, wherein the process is carried out in an inert solvent.

10. The process according to claim 9, wherein the inert solvent is dimethylformamide (DMF).

11. The process according to claim 1, wherein the process is carried out at a temperature of from 0° C.-100° C.

12. A compound of formula (II"):

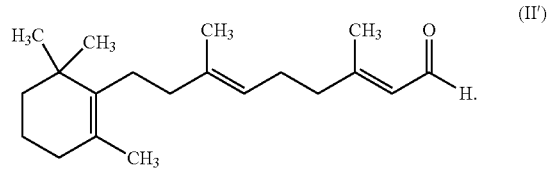

(II')

13. A compound of formula (II"):

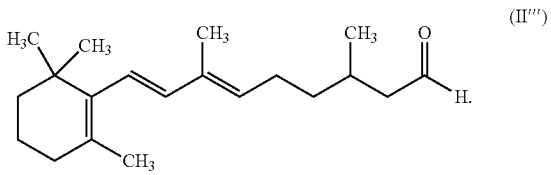

(II''')

14. A compound of formula (III):

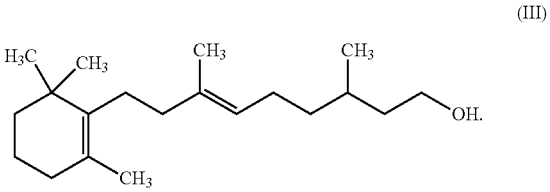 [SMILES: CC1=C(CC/C(C)=C/CCC(C)CCO)C(C)(C)CCC1]

(III)

* * * * *